United States Patent [19]
Edens et al.

[11] Patent Number: 5,943,632
[45] Date of Patent: *Aug. 24, 1999

[54] METHOD AND APPARATUS FOR DETECTING AND DISPLAYING IRREGULARITIES IN FERROUS PIPE

[75] Inventors: Brian Wade Edens; Chester Wayne Pape, both of San Antonio, Tex.

[73] Assignee: Oilfield Equipment Marketing, Inc., San Antonio, Tex.

[ * ] Notice: This patent is subject to a terminal disclaimer.

[21] Appl. No.: 08/661,315

[22] Filed: Jun. 13, 1996

Related U.S. Application Data

[63] Continuation-in-part of application No. 08/521,406, Aug. 30, 1995, Pat. No. 5,671,155.
[51] Int. Cl.[6] .................................................. G01N 27/00
[52] U.S. Cl. ............................................. 702/38; 324/263
[58] Field of Search ..................................... 364/507, 484, 364/485; 324/263, 220, 235, 238, 240, 237, 227, 228, 212; 702/38, 36, 35

[56] References Cited

U.S. PATENT DOCUMENTS

| | | | |
|---|---|---|---|
| 4,602,212 | 7/1986 | Hiroshima et al. | 324/227 |
| 4,934,179 | 6/1990 | Biggerstaff | 73/40.5 R |
| 5,140,265 | 8/1992 | Sakiyama et al. | 324/220 |
| 5,256,965 | 10/1993 | Nomura | 324/212 |
| 5,619,136 | 4/1997 | Drury | 324/242 |
| 5,671,155 | 9/1997 | Edens et al. | 364/507 |

*Primary Examiner*—Melanie A. Kemper
*Attorney, Agent, or Firm*—Christopher L. Makay

[57] ABSTRACT

An apparatus for detecting irregularities in a ferrous pipe includes a magnetizing coil for inducing a magnetic field in the ferrous pipe. Inspection sensors measure changes in the induced magnetic field and produce signals representative of those changes. An analog-to-digital converter digitizes the measured signals representing the changes in the induced magnetic field. A processor compares the signals to a threshold value, and, when a signal exceeds the threshold value, the processor stops the inspection process to locate an irregularity in the ferrous pipe. The processor further processes the signals according to frequency to classify the signals by type of irregularity in the ferrous pipe. A screen and/or printer displays the frequency processed signals according to type of irregularity in the ferrous pipe.

40 Claims, 13 Drawing Sheets

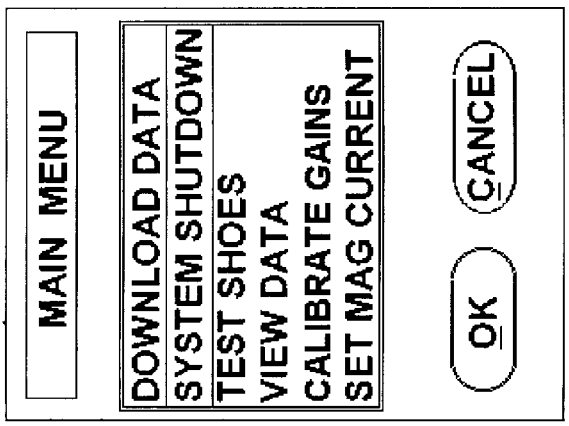
FIGURE 10A
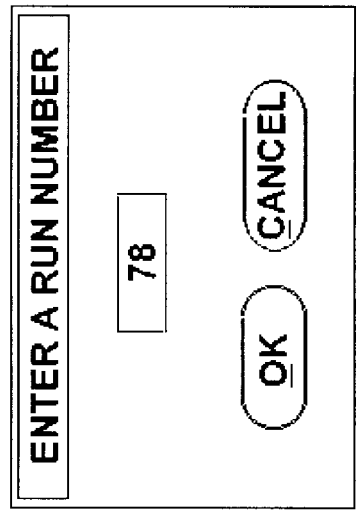
FIGURE 10B
FIGURE 10C
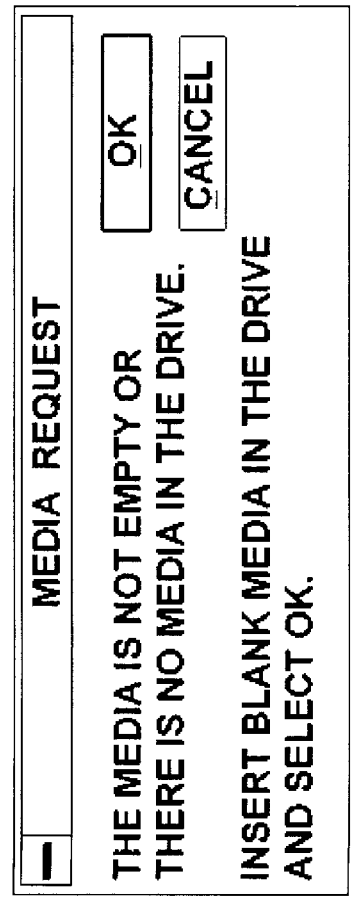
FIGURE 10D

METHOD AND APPARATUS FOR DETECTING AND DISPLAYING IRREGULARITIES IN FERROUS PIPE

CROSS REFERENCE TO RELATED APPLICATIONS

This application is a continuation-in-part of U.S. Ser. No. 08/521,406 filed Aug. 30, 1995, now U.S. Pat. No. 5,671,155 which issued Sep. 23, 1997 to Edens et al.

BACKGROUND OF THE INVENTION

1. Field of the Invention

The present invention relates to detecting and displaying irregularities in ferrous pipe and, more particularly, but not the way of limitation, to a method and apparatus that employs digital signal processing techniques to produce extremely accurate representations of the irregularities.

2. Description of the Related Art

Ferrous pipe is used in a variety of applications such as the drill string of a well drilling system. Such pipe must be inspected for defects after formation and periodically during use to determine if service induced flaws exist. A pipe containing a flaw such as a crack or loss of metallic area is susceptible to rupturing which results in unnecessary labor as well as a potentially dangerous situation. Accordingly, various systems have been developed to detect flaws in ferrous pipe so that the pipes may be repaired or discarded before rupturing.

Typical systems induce a magnetic field in a ferrous pipe which is then sensed by a bank of magnetic field sensors such as search coils. A motorized mechanical device propels the magnetic field sensors along the length of the pipe or the sensors remain stationary while the pipe feeds past the sensors. The sensors pick up the changes in the magnetic field caused by flaws and produce signals representative of those changes. An analog processing system inputs the magnetic field signals and filters them to remove noise. The analog processor then prints those signals on a strip chart as a one dimensional graph. Spikes on the strip chart which represent large changes in magnetic flux indicate flaws in the pipe. Accordingly, after the printing of the strip chart, a system operator can try to match the chart to the pipe in an attempt to locate the suspected flaw using any of a variety of prove-up methods.

Although the analog signal processor produces usable information indicating the location of flaws in ferrous pipe, it suffers from several disadvantages. First, analog signal processing limits the amount of information available to the user. Illustratively, an analog signal processor does not provide frequency information because it cannot determine frequency without continuous user monitoring. Such user monitoring would diminish inspection speed to a point where it would be economically unfeasible. Finally, an analog signal processor does not provide discrete values representing flaws which makes locating flaws as well as determining their severity difficult. Consequently, unflawed pipe is often unnecessarily discarded, while flawed pipe might be used.

U.S. Pat. No. 5,030,911 which issued Jul. 9, 1991 to Lam discloses a tester for new pipes that uses digital signal processing in an attempt to improve over analog signal processing. The Lam tester includes search coils that traverse a pipe to detect changes in a magnetic field induced in the pipe. A digital computer digitizes and processes the magnetic field information for display on a two dimensional plot. The processing performed by the computer consists of threshold or signal magnitude evaluation. To perform the threshold evaluation, an operator inputs a threshold value which the computer then compares to the incoming signals. The computer processes any signal with a magnitude above the threshold and does not process any signal below the threshold. The computer prints the stored signals on a two dimensional plot representing the circumference of the pipe to provide an indication of defects. The Lam tester provides a second graph below the first graph to display the digital equivalent of all the analog values input into the computer. Consequently, the second graph consists of the digitized versions of the analog signals with no additional processing. An operator then uses the two graphs in tandem to determine where defects exist along the new pipe tested.

Although the Lam new pipe tester includes a computer for digital signal processing, it does not provide real time processing because the two dimensional plot cannot be generated until the entire length of the pipe has been scanned. Furthermore, the Lam system only performs threshold evaluation and does not perform any other type of processing such as frequency analysis. Without additional processing, the computer fails to properly eliminate noise from the magnetic field signals resulting in false indications of pipe flaws. Thus, it is often time consuming to locate flaws because a complete manual inspection of the pipe must be performed to distinguish real flaws from false indications. Consequently, the Lam tester is limited to the detection of flaws in new pipes and is unable to analyze used pipe.

Accordingly, a method and apparatus that performs digital signal processing and analysis in conjunction with improved magnetic field detection to precisely indicate and quickly locate flaws would significantly improve over the above described systems because it makes the inspection of both new and used ferrous pipe possible while reducing defect location time to a minimum.

SUMMARY OF THE INVENTION

In accordance with the present invention, a pipe tester for detecting irregularities in a ferrous pipe includes a magnetizing coil for inducing a magnetic field in the ferrous pipe. Sensors housed in inspection shoes measure changes in the induced magnetic field and produce signals representative of those changes. A drive unit propels the magnetizing coil and inspection shoes along the ferrous pipe. An analog-to-digital converter digitizes the signals to produce machine readable data.

A direct memory access controller handles the storage of the digitized signals in a random access memory. A processor inputs those signals and compares the signals to a first threshold value, and, when a signal exceeds the threshold value, the processor stops the inspection process to locate an irregularity in the ferrous pipe. The processor further processes the signals according to frequency to classify the signals by type of irregularity in the ferrous pipe. The processor additionally scales the signals, applies a gain factor to the signals, and eliminates any signals less than a second threshold value. After completing the analysis of the signals, the processor displays the analyzed signals according to type of irregularity in the ferrous pipe.

It is, therefore, an object of the present invention to provide a pipe tester that employs digital signal processing techniques to accomplish ferrous pipe testing in real time.

It is a another object of the present invention to employ frequency analysis to permit the classification of irregularities according to type.

It is a further object of the present invention to provide means for stopping the inspection process to locate an irregularity in the ferrous pipe.

Still other objects, features, and advantages of the present invention will become evident to those of ordinary skill in the art in light of the following.

BRIEF DESCRIPTION OF THE DRAWINGS

FIGS. 10A–D illustrate control panels displayed to the user on the screen of the pipe tester.

DETAILED DESCRIPTION OF THE PREFERRED EMBODIMENT

Figure 1:
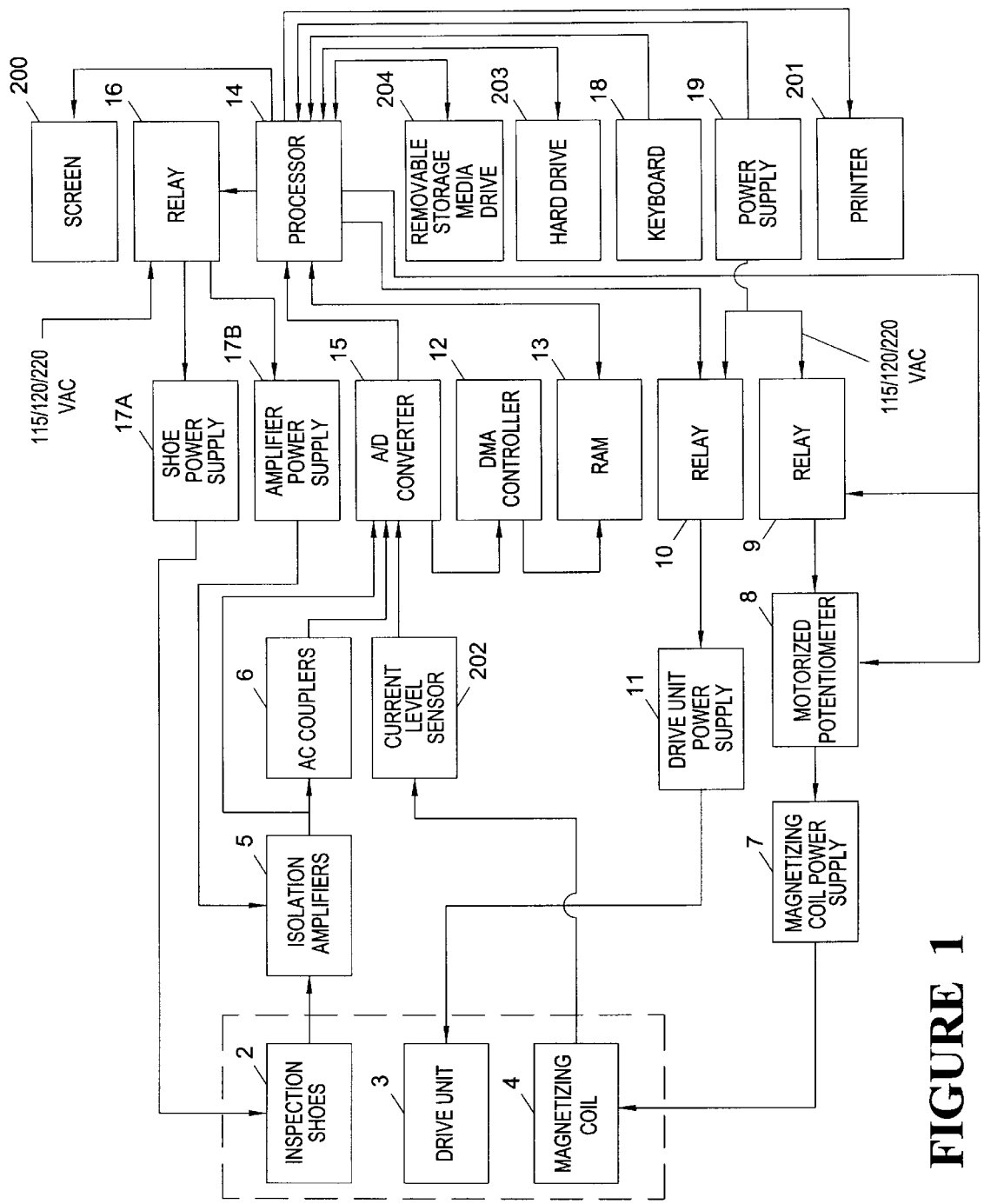
FIG. 1 is a block diagram illustrating the hardware components of the pipe tester.
Figure 2:
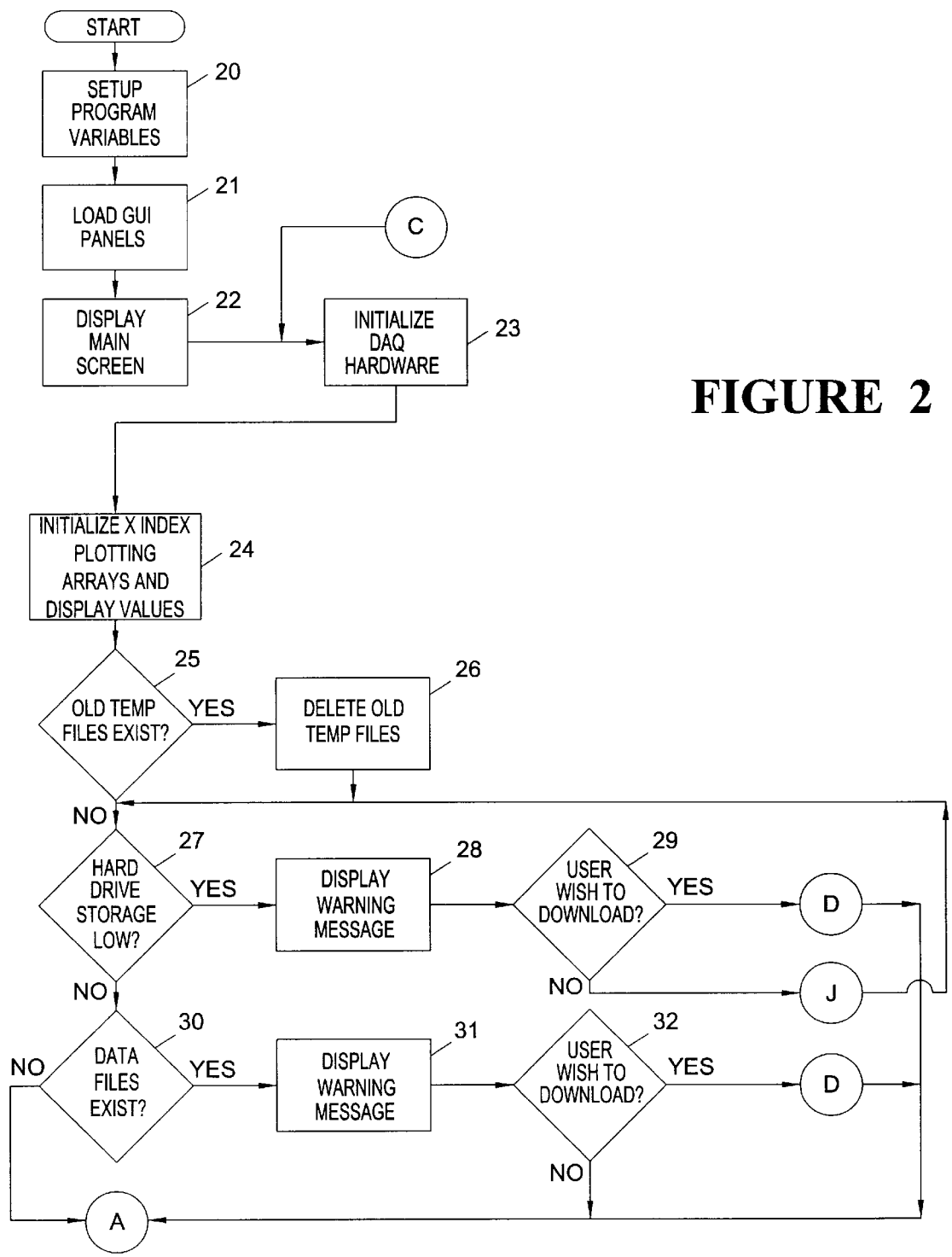
FIG. 2 is a flow chart illustrating the initialization routine for the computer of the pipe tester.

Referring to FIG. 1, pipe tester 1 includes an inspection tool which may be any device capable of inducing a magnetic field in a ferrous pipe and then measuring changes in that magnetic field. Such an inspection tool is manufactured by Oilfield Equipment Marketing, Inc. which has a place of business at 4711 Dodge Street, San Antonio, Tex. 78217.

The inspection tool includes inspection shoes 2 which contain magnetic field sensors, drive unit 3, and magnetizing coil 4. In this preferred embodiment, the magnetic field sensors are groups of individual linear Hall magnetic field transducers, however, one of ordinary skill in the art will realize that other types of magnetic field sensors may be used. Drive unit 3 includes motors (not shown) that each drive an individual roller in a system of rollers (not shown). In this preferred embodiment, the motors are high torque DC motors, however, one of ordinary skill in the art will recognize that AC motors may be used. Each individual roller mounts within a frame of the inspection tool in a position that permits contact with the pipe. Processor 14 controls relay 10 in accordance with user input to alternately connect and disconnect drive unit power supply 11 with a standard power source such as a 115/120 VAC or 220 VAC line to provide the DC motors with their required DC voltage levels. With drive unit power supply 11 connected to the 115/120 VAC source, drive unit 3 propels the inspection tool along the pipe.

Magnetizing coil 4 mounts onto the inspection tool frame to induce a magnetic field in the pipe. Processor 14 controls relay 9 to alternately connect and disconnect magnetizing coil power supply 7 with a standard power source such as 115/120 VAC or 220 VAC line to provide magnetizing coil 4 with its required DC voltage level. Processor 14 further controls motorized potentiometer 8 in accordance with user input or a default value to regulate the current that magnetizing coil power supply 7 delivers to magnetizing coil 4.

Pipe tester 1 includes current level sensor 202 to monitor the level of the current in magnetizing coil 4 and produce a signal representative of that current level. Current level sensor 202 inputs the magnetizing coil current level and outputs a voltage corresponding to that current. Analog to digital A/D converter 15 digitizes the voltage signal to furnish processor 14 with a signal for comparison with the user input or default magnetizing current level value. Processor 14 then utilizes the result of the comparison to control motorized potentiometer 8 and adjust the current level in magnetizing coil 4 to the user input or default value.

Inspection shoes 2 mount circumferentially within the inspection tool frame to ensure that the individual linear Hall transducers provide greater than 100% surface area coverage of the pipe. Additionally, inspection shoes 2 mount longitudinally with respect to the pipe axis to detect longitudinally oriented defects. The individual linear Hall transducers measure changes in a magnetic field induced in the pipe and produce voltage signals proportional to the intensity of that change. When the inner and outer surfaces of the pipe are completely uniform, the magnetic field induced by magnetizing coil 4 remains constant, however, irregularities whether internal or external of the pipe create variances in the magnetic field. Typical irregularities include transversely oriented flaws such as fatigue cracks, pits, and inclusions and longitudinally oriented flaws such as laps, seams, weld line hook cracks, and quench cracks. Irregularities further typically include wall loss which may be localized or full length eccentric such as rod wear, fluid erosion, and mandrel drift. The linear Hall transducers detect those changes and produce a voltage with the magnitude corresponding to the magnitude of the flaw or wall loss.

Typically, inspection shoes 2 include a number of individual linear Hall transducers with the actual number of transducers dependent upon the diameter of the pipe inspected. Illustratively, a pipe having a diameter of 5.5 inches requires eight inspection shoes to provide a total of 136 individual linear Hall transducers. Additionally, separate sets of inspection shoes for the detection of flaws and wall loss may be utilized although, in this preferred embodiment, only a single set of inspection shoes containing magnetic field sensors oriented parallel to the pipe surface is utilized because processor 14 processes the magnetic field data such that the wall loss information is separated from the flaw information. In this preferred embodiment, the inspection tool traverses the pipe to produce the magnetic field data, however, one of ordinary skill in the art will recognize that the inspection tool may remain stationary while the pipe is fed past or rotated about inspection shoes 2.

Pipe tester 1 includes isolation amplifiers 5, which in this preferred embodiment are unity gain operational amplifiers, to buffer the magnetic field data signals generated by inspection shoes 2. The number of isolation amplifiers 5 corresponds to the number of inspection shoes 2 or individual linear Hall transducers. Shoe power supply 17A provides the individual linear Hall transducers of inspection shoes 2 with their required DC voltage level, while amplifier power supply 17B provides isolation amplifiers 5 with their required DC voltage level. Processor 14 controls relay 16 in accordance with user input to alternately connect and disconnect both shoe power supply 17A and amplifier power supply 17B with a standard power source such as a 115/120 VAC or 220 VAC line.

Pipe tester 1 includes AC couplers 6 to block any DC component of the magnetic field data signals output from the linear Hall sensors. AC couplers 6 are a capacitive bank having a number of capacitors equal to the number of individual linear Hall transducers or inspection shoes 2.

Pipe tester 1 includes a digital computer to process the magnetic field data signals output from inspection shoes 2 and determine any wall loss or flaws in the inspected pipe. In this preferred embodiment, the computer includes processor 14, analog-to-digital (A/D) converter 15, random access memory (RAM) 13, direct memory access (DMA) controller 12, hard drive (HD) 203, removable storage media drive 204 (e.g. disk drive, tape drive, optical drive, etc.), keyboard 18, power supply 19, screen 200, and printer 201. Power supply 19 connects to a standard power source such as a 115/120 VAC or 220 VAC line to provide the DC voltage levels required by the computer. Processor 14 may be any suitable microprocessor. A/D converter 15 digitizes the magnetic field data signals output from inspection shoes 2 and the current level signal output from current level sensor 202 to provide machine readable signals for DMA controller 12, RAM 13, and processor 14. RAM 13 stores the digitized magnetic field data signals both prior to and after processing by computer 14. HD 203 and removable storage media in removable storage media drive 204 provide long term storage of the processed magnetic field data signals. Keyboard 18 connects to processor 14 to permit user input and system control, while screen 200, which may be any suitable display device such as a cathode ray tube or liquid crystal display, depict the system controls, the wall loss graph, and the flaw graph. Printer 201 provides the user with a hard copy of the display from screen 200. DMA controller 12 handles the storing of the digitized magnetic field data signals in RAM 13. That handling of data storage using DMA controller 12 frees processor 14 to process the current block of stored magnetic field data signals. Thus, the computer performs real time analysis of the magnetic field data signals because processor 14 does not have to perform the task of data storage to RAM 13.

Referring to FIGS. 2–8, the operation of the computer, particularly processor 14, to control the inspection tool and process the magnetic field data signals for display will be described. To initiate testing, a user plugs the computer into a standard power source such as a 115/120 VAC or 220 VAC, turns the computer on, and places the inspection tool around a ferrous pipe. With power applied to the computer, processor 14 executes step 20 to initialize (i.e., set to 0) the program variables. In this preferred embodiment, the program variables include magnetic field data signals, wall loss high signal value, wall loss high signal channel (i.e., the channel of particular inspection shoe containing the linear Hall transducer providing the largest wall loss signal), flaw high signal value, flaw high signal channel (i.e., the channel of particular inspection shoe containing the linear Hall transducer providing the largest flaw signal), motor speeds and direction, magnetizing coil current level, signal level control values, gain factors, Auto Stop value, x-index counter, shoe and amplifier power supply indicator, and magnetizing coil power supply indicator.

Processor 14 proceeds to step 21 and loads from HD 203 the panels illustrated in FIGS. 10A–F and FIG. 11. In step 22, processor 14 displays the main screen shown in FIG. 11, except the wall loss and flaw detection graphs contain no plotted points. Processor 14 in step 23 initializes the data acquisition (DAQ) hardware by setting all voltage input, output, and digital input/output I/O channels to 0 volts and all digital bits to a logical 0. The data acquisition hardware includes A/D converter 15, RAM 13, and DMA controller 12.

In step 24, processor 14 initializes (i.e., sets to 0) an X-index counter which indicates the latest sampling interval processed and displayed by processor 14. The X-axis of the wall loss and flaw detection graphs represents a calculated time interval of consecutive real time data sampling periods (15 seconds in this preferred embodiment). In this preferred embodiment, the sampling periods performed by processor 14 are 134 milliseconds. When the X-index counter equals the calculated time interval, processor 14 saves the graphed wall loss and flaw data and begins new wall loss and flaw detection graphs. The Y-axis of the wall loss and flaw detection graphs represents a scaled unitless signal level relative to a calibration defect signal and corresponding to the measured magnetic field data signals.

After processor 14 completes initialization steps 20–24, it proceeds to step 25 and determines whether old temporary files exists in HD 203. If old temporary files exist, processor 14 deletes those files in step 26 before proceeding to step 27, otherwise, processor 14 proceeds directly to step 27.

In step 27, processor 14 determines if HD 203 has sufficient storage space remaining for a pipe test. If available space is less than 5 megabytes in this preferred embodiment, processor 14 proceeds to step 28 and displays a message informing the user that insufficient storage space exists. Processor 14 then proceeds to step 29 and queries the user whether they wish to download files to removable storage media in drive 204. If the user elects to download files, processor 14 proceeds to routine D which will be described herein with reference to FIG. 5. After completing routine D, processor 14 proceeds to routine A which is described herein with reference to FIG. 3. Alternatively, if the user elects not to download files, processor 14 proceeds to routine J which is described herein with reference to FIG. 6. After completing routine J, processor 14 returns to step 27.

If HD 203 contains sufficient capacity, processor 14 proceeds to step 30 and determines whether data files exist. When processor 14 determines data files exist in HD 203, it displays in step 31 a warning message to the user. That warning provides the user with the option of downloading the existing files to removable storage media in drive 204 for later use. In step 32, processor 14 queries the user whether they wish to download the existing files. If the user elects not to download the files, the files will remain in HD 203 and processor 14 proceeds to routine A which will be described herein with reference to FIG. 4. When the user elects to download the files, processor 14 proceeds to routine D which will be described herein with reference to FIG. 5. After completing routine D, processor 14 proceeds to routine A which is described herein with reference to FIG. 3.

Figure 3:
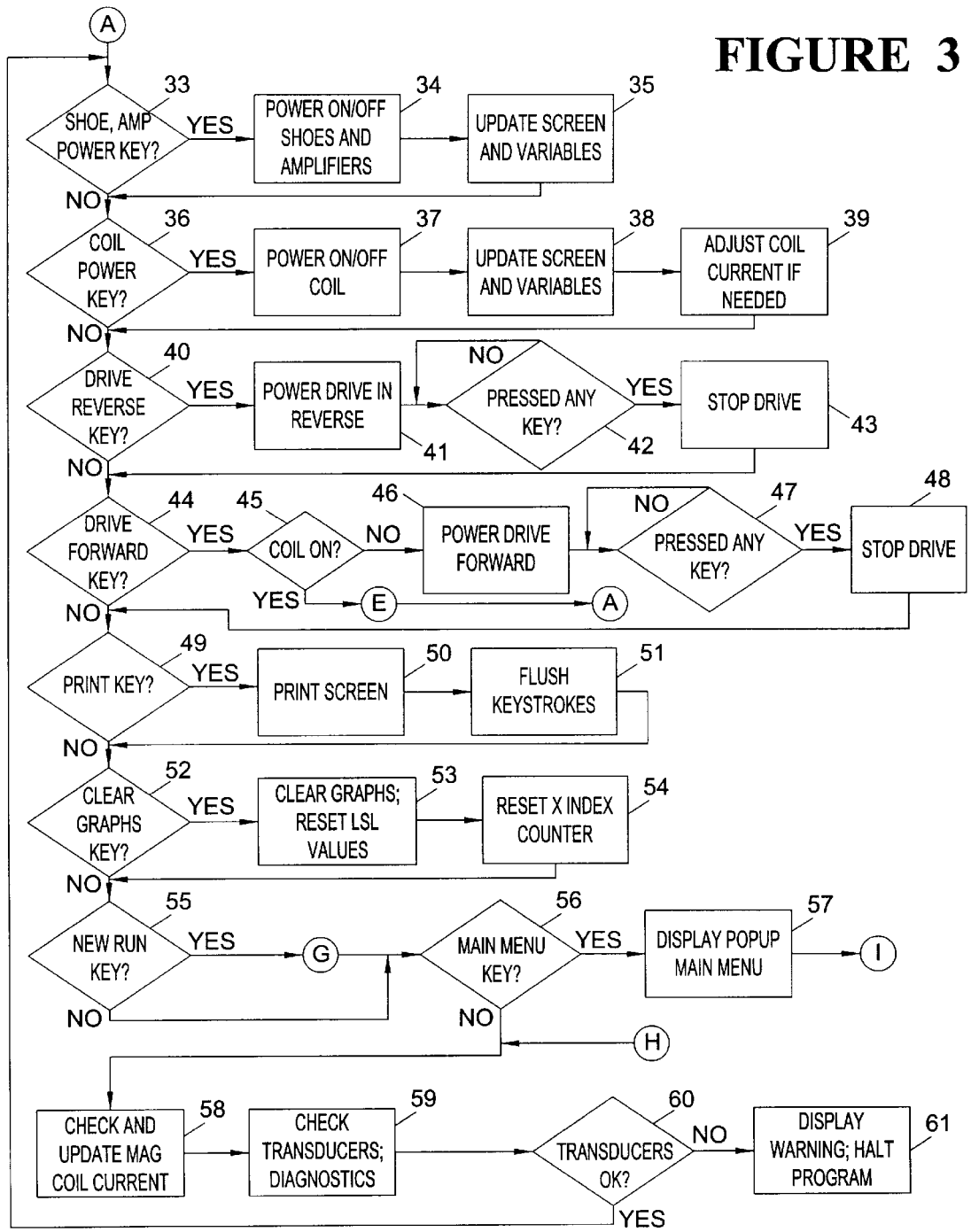
FIG. 3 is a flow chart illustrating the system control routine for the computer of the pipe tester.

Referring to FIG. 3, processor 14 begins routine A by executing step 33 which consists of determining if the user has pressed the shoe/amplifier power key. In this preferred embodiment, the user activates and deactivates shoe and amplifier power supplies 17A and 17B by pressing the ALT key in combination with the A key. When processor 14 determines the shoe/amplifier power key has been pressed, it executes step 34, otherwise, it proceeds directly to step 36. If the power is off, processor activates relay 16 to connect shoe power supply 17A and amplifier power supply 17B to the standard power source. Conversely, if the power is on, processor deactivates relay 16 to disconnect shoe power supply 17A and amplifier power supply 17B from the standard power source. In step 35, processor 14 updates the shoe/amplifier power supply indicator variable and displays on screen 200 whether those power supplies are on or off (see reference numeral 300 in FIG. 11).

In step 36, processor 14 determines if the user has pressed the magnetizing coil power key. In this preferred embodiment, the user activates and deactivates magnetizing coil 4 by pressing the ALT key in combination with the M key or, alternatively, the function key F9. When processor 14 determines the magnetizing coil key has been pressed, it executes step 37, otherwise, it proceeds directly to step 40. If magnetizing coil 4 is off, processor activates relay 9 to connect magnetizing coil power supply 7 to the standard power source. Conversely, if the power is on, processor deactivates relay 9 to disconnect magnetizing coil power supply 7 from the standard power source. In step 35, processor 14 updates the magnetizing coil power supply indicator variable and displays on screen 200 whether magnetizing coil power supply 7 is on or off (see reference numeral 301 in FIG. 11). Processor 14 then proceeds to step 39 and determines if the current level within magnetizing coil 4 equals the user input or default current level. If the actual value as measured by current level sensor 202 does not equal the user input or default level, processor 14 outputs a signal that controls motorized potentiometer 8. That signal manipulates motorized potentiometer 8 and, thus, its resistance value to either increase or decrease the current output from magnetizing coil power supply 7.

In step 40, processor 14 determines if the user has depressed the drive unit reverse key. In this preferred embodiment, the reverse arrow key on keyboard 18 serves as the drive unit reverse key. If the user has not depressed the drive unit reverse key, processor 14 proceeds to step 44, otherwise, processor 14 proceeds to step 41. Processor 14 executes step 41 by activating relay 10 to connect drive unit power supply 11 to the standard power source. In the reverse mode, processor 14 activates relay 10 such that drive unit power supply 11 supplies a negative voltage to drive unit 3 resulting in drive unit 3 driving the inspection tool in reverse. Processor 14 sustains relay 10 activated until it determines in step 42 that the user has depressed any key on keyboard 18. Once the user depresses any key, processor 14 executes step 43 by deactivating relay 10 thereby stopping the reverse movement of the inspection tool.

In step 44, processor 14 determines if the user has depressed the drive unit forward key. In this preferred embodiment, the forward arrow key on keyboard 18 serves as the drive unit forward key. If the user has not depressed the drive unit forward key, processor 14 proceeds to step 49, otherwise, processor 14 proceeds to step 45. Processor 14 executes step 45 by determining if the user has powered on magnetizing coil 4. If magnetizing coil has been powered on, processor 14 executes routine E which is described herein with reference to FIG. 9, otherwise, processor 14 proceeds to step 46. Processor 14 executes step 46 by activating relay 10 to connect drive unit power supply 11 to the standard power source. In the forward mode, processor 14 activates relay 10 such that drive unit power supply 11 supplies a positive voltage to drive unit 3 resulting in drive unit 3 driving the inspection tool forward. Processor 14 sustains relay 10 activated until it determines in step 47 that the user has depressed any key on keyboard 18. Once the user depresses any key, processor 14 executes step 48 by deactivating relay 10 thereby stopping the forward movement of the inspection tool.

In step 49, processor 14 determines if the user desires to print using printer 201 the wall loss and flaw detection graphs currently displayed on screen 200. In this preferred embodiment, the user selects the print option by pressing the ALT key in combination with the P key. If the user has not elected to print, processor 14 proceeds to step 52, otherwise, processor 14 proceeds to step 50. Processor 14 executes step 50 by downloading the screen displayed on screen 200 (see FIG. 11) to printer 201 for printing. In step 51, processor 14 flushes the keyboard buffer of keyboard 18 so that any inadvertent key depressions will not affect the screen print.

In step 52, processor 14 determines if the user desires to erase the wall loss and flaw detection graphs currently displayed on screen 200. In this preferred embodiment, the user selects the graph erase option by pressing the ALT key in combination with the E key. If the user has not elected to erase the graphs, processor 14 proceeds to step 55, otherwise, processor 14 proceeds to step 53. Processor 14 executes step 53 by removing the wall loss and flaw detection graphs currently displayed on screen 200. Processor 14 further resets the wall loss high signal value, flaw high signal value, wall loss high signal channel, and flaw high signal channel variables to 0 (described herein). In step 54, processor 14 resets the X-index counter to 0 before proceeding to step 55.

In step 55, processor 14 determines if the user desires to begin a new run which is the forward movement of the inspection tool along the pipe in combination with the collection and processing of magnetic field data. In this preferred embodiment, the user selects the new run option by pressing the ALT key in combination with the N key. If the user has not elected to begin a new run, processor 14 proceeds to step 56, otherwise, processor 14 executes routine G which is described herein with reference to FIG. 7. After executing routine G, processor 14 returns and executes step 56.

In step 56, processor 14 determines if the user desires to display the main menu. In this preferred embodiment, the user selects to display the main menu by pressing the function key F12. If the user elects not to display the main menu, processor 14 proceeds to step 58, otherwise, processor 14 proceeds to step 57. Processor 14 executes step 57 by displaying on screen 200 the main menu depicted in FIG. 10A. Main menu 10A provides the user with the options of downloading data, shutting pipe tester 1 down, testing the linear Hall transducers, viewing data from a prior pipe test, calibrating the gain level to determine the gain factor for each linear Hall transducer, or setting the current level for magnetizing coil 4. After displaying the main menu depicted in FIG. 10A on screen 200, processor 14 executes routine I which is described herein with reference to FIG. 4.

In step 58, processor 14 evaluates and updates, if necessary, the level of current flowing through magnetizing coil 4. Processor 14 inputs the actual current level measured by current level sensor 202 and compares that value to the user input or default current level. If the actual current level does not equal the user input or default level, processor 14 outputs a signal that controls motorized potentiometer 8. That signal manipulates motorized potentiometer 8 and, thus, its resistance value to either increase or decrease the current output from magnetizing coil power supply 7.

In step 59, processor 14 determines if one or more linear Hall transducers is defective. Processor 14 executes step 59 by inputting from A/D converter 15 magnetic field data signals that have not passed through AC couplers 6 and, therefore, have not been stripped of their DC component.

After inputting the magnetic field data signals including their DC component, processor 14 in step 60 compares each digitized DC component to an expected quiescent value for linear Hall transducers to determine which, if any, of the linear Hall transducers are defective. When no defective linear Hall transducers are found, processor 14 re-executes routine A. However, when at least one linear Hall transducer is diagnosed as defective, processor 14 executes step 61 by stopping the execution of routine A and displaying a message informing the user that a defective linear Hall transducer exists. Processor 14 further displays a message to the user providing the location of the defective linear Hall transducer in inspection shoes 2. Processor 14 will halt program execution and only continue after the replacement of the defective linear Hall transducer(s) followed by the re-initialization of the computer.

Figure 4:
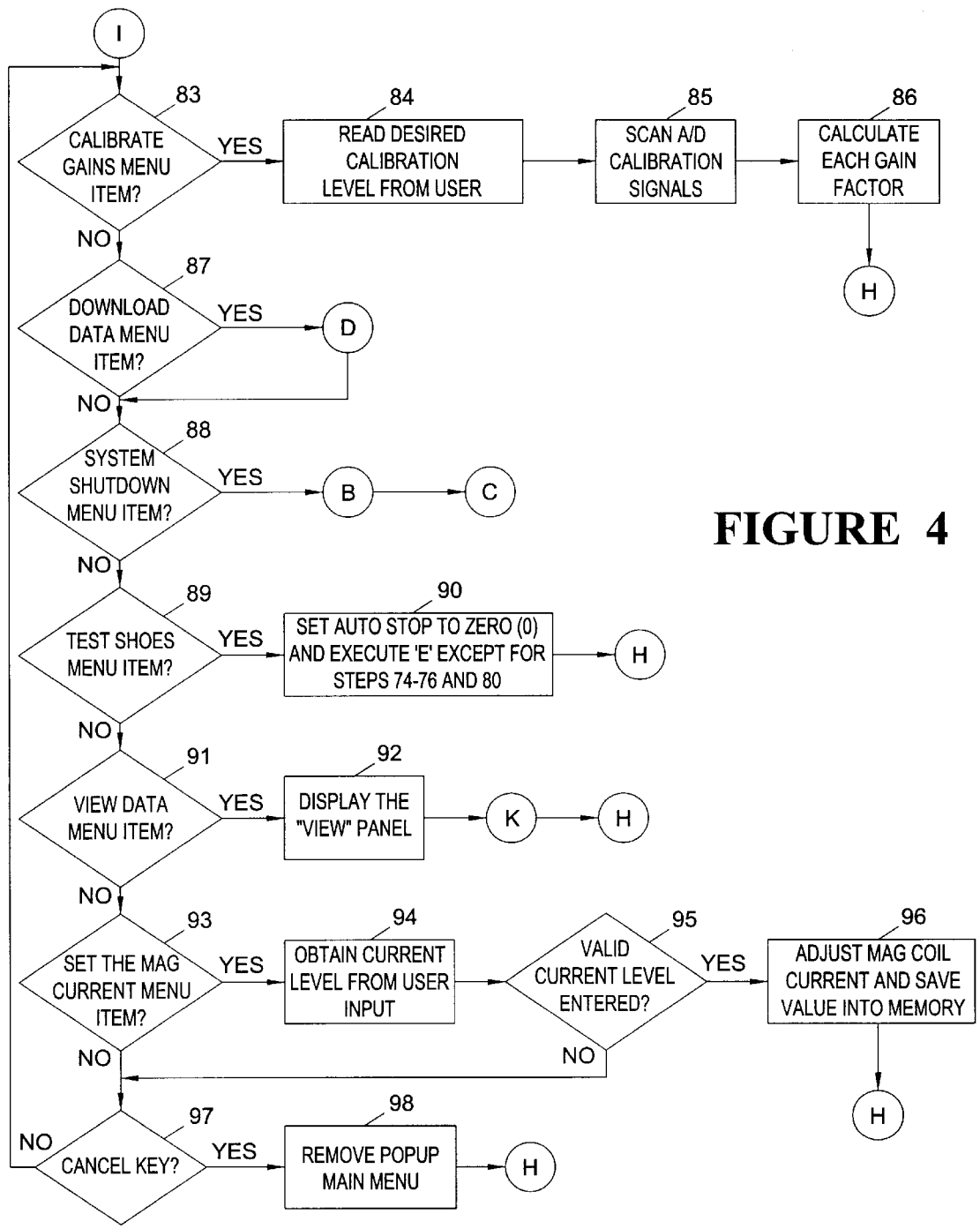
FIG. 4 is a flow chart illustrating the main menu routine for the computer of the pipe tester.

Referring to FIG. 4, processor 14 executes routine I after displaying in step 57 the main menu illustrated in FIG. 10A. With the main menu displayed on screen 200, the user may select any one of the listed options by manipulating the up and down arrow keys on keyboard 18 and selecting the OK prompt. In this preferred embodiment, the user selects the OK prompt by depressing the ALT key in combination with the O key. Similarly, the user selects the CANCEL prompt by depressing the ALT key in combination with the C key.

In step 83, processor 14 determines if the user elected to calibrate the gain level for each linear Hall transducer. If the user elects not to calibrate the gain level, processor 14 proceeds to step 87, otherwise, processor 14 proceeds to step 84. Processor 14 must calibrate the gain level (i.e., determine a gain factor) for each signal from the linear Hall transducer because the outputs from those transducer will vary from one to the other due to manufacturing tolerances. To determine an appropriate gain factor for each linear Hall transducer, processor 14 in step 84 prompts the user to enter a desired signal output level. The individual linear Hall transducers are then passed over a known flaw so that measured magnetic field data signals are developed. In step 85, processor 14 inputs the digitized magnetic field data signals from A/D converter 15. Processor 14 then executes step 86 to calculate the gain factor for each linear Hall transducer. Processor 14 calculates the gain factor by dividing the desired signal output level by each measured magnetic field data signal to produce a ratio for each linear Hall transducer which is then utilized to adjust subsequent measured signals. Processor 14 then proceeds to routine H and executes steps 58, 59, 60 and possibly 61 as previously described with reference to FIG. 3.

In step 87, processor 14 determines if the user has elected to download data from HD 203 to removable storage media in drive 204. If the user does not wish to download data, processor 14 proceeds to step 88, otherwise, processor 14 executes routine D which is described herein with reference to FIG. 5 before proceeding to step 88. Processor 14 executes step 88 by determining if the user has elected to shut down pipe tester 1. If the user does not elect to shut down pipe tester 1, processor 14 proceeds to step 89. Conversely, when the user elects to shut down pipe tester 1, processor 14 executes routine B which is described herein with reference to FIG. 6 followed by routine C as previously described with reference to FIG. 2.

In step 89, processor 14 determines if the user has elected to test the linear Hall transducers. When the user elects not to test, processor 14 proceeds to step 91, otherwise, processor 14 sets the Auto Stop value to zero and executes routine E except for steps 74–76 and 80 and then returns to the calling routine. Processor 14 then proceeds to routine H and executes steps 58, 59, 60, and possibly 61 as previously described with reference to FIG. 3.

In step 91, processor 14 determines if the user has elected to view previously measured wall loss and flaw detection data. If the user elects not to view data, processor 14 proceeds to step 93, otherwise, processor 14 executes step 92 to display on screen 200 the "view" panel illustrated in FIG. 10E. Processor 14 then executes routine K which is described herein with reference to FIG. 8. When processor 14 finishes routine K, it exits to routine H and executes steps 58, 59, 60 and possibly 61 as previously described with reference to FIG. 3.

In step 93, processor 14 determines if the user desires to adjust the current level in magnetizing coil 4. If the user elects not to adjust the current level in magnetizing coil 4, processor 14 proceeds to step 97. After processor 14 determines the user desires to adjust the magnetizing coil current, it proceeds to step 94 and prompts the user to input a new current for magnetizing coil 4. In step 95, processor 14 determines if the input current level is valid. A current level is valid if it does not exceed the maximum current level of magnetizing coil 4. After receiving the new current level for magnetizing coil 4, processor 14 in step 98 saves that value in its memory. Processor 14 then adjusts the level of current supplied to magnetizing coil 4 as previously described with reference to FIGS. 1 and 3. Processor 14 then proceeds to routine H and executes steps 58, 59, 60 and possibly 61 as previously described with reference to FIG. 3.

Processor 14 performs step 97 to determine if the user desires to exit the main menu. In this preferred embodiment, the user selects the CANCEL key by depressing the ALT key in combination with the letter C. If the user does not elect to exit routine I, processor 14 returns to step 83, otherwise, processor 14 proceeds to step 98. Processor 14 executes step 98 by removing the main menu from screen 200 and proceeding to routine H which consists of executing steps 58, 59, 60, and possibly 61 as previously described with reference to FIG. 3.

Figure 5:
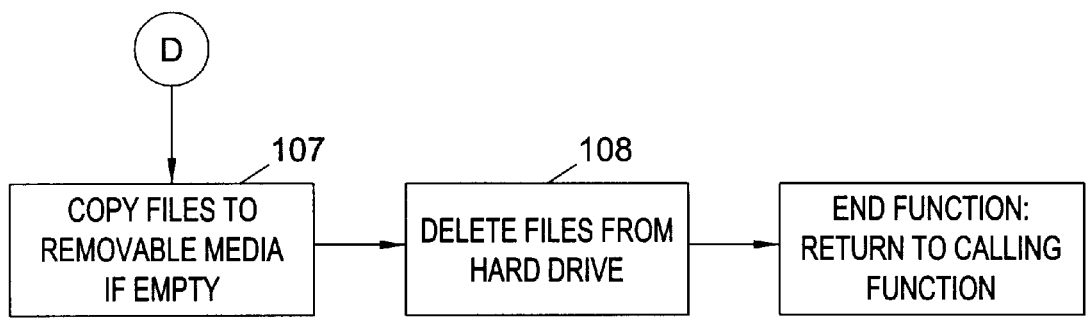
FIG. 5 is a flow chart illustrating the magnetic field data storage routine for the computer of the pipe tester.

Referring to FIG. 5, processor 14 begins routine D by displaying the panel illustrated in FIG. 10B. In this preferred embodiment, the user selects the OK prompt by depressing the ALT key in combination with the 0 key. Similarly, the user selects the CANCEL prompt by depressing the ALT key in combination with the C key. If the user selects the CANCEL prompt, processor 14 returns to the routine from which routine D was called. Once the user selects OK, processor 14 determines if removable storage media resides in drive 204 and whether information exists of the media. If information exists on the media or no media resides in drive 204, processor 14 displays the panel illustrated in FIG. 10C. If the user selects the CANCEL prompt, processor 14 returns to the routine from which routine D was called. However, if the user selects the OK prompt and the media resides in drive 204, processor 14 executes step 107 by copying the selected files from HD 203 onto the media. In step 108, processor 14 deletes all the selected files from HD 203 and returns to the routine from which routine D was called.

Figure 6:
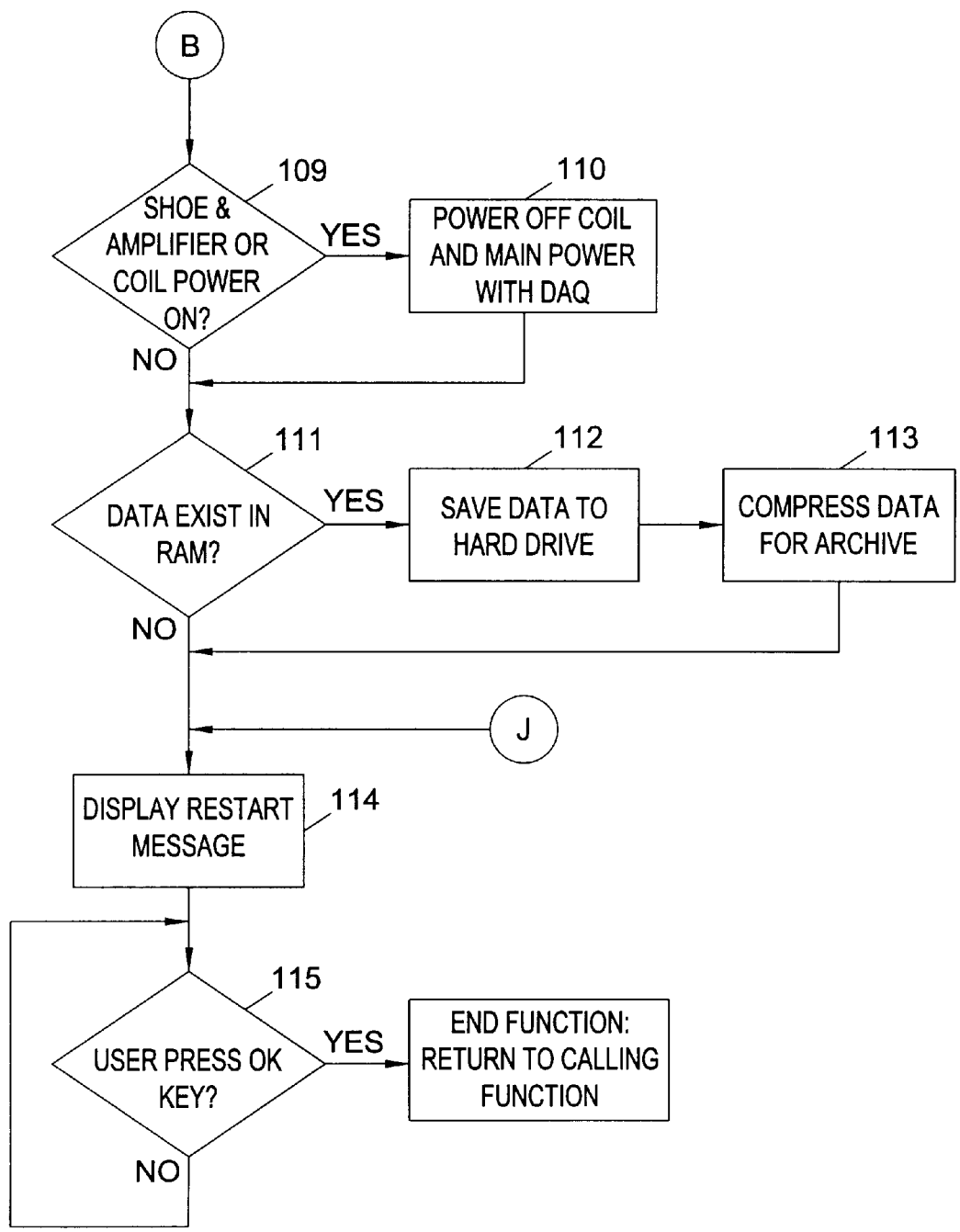
FIG. 6 is a flow chart illustrating the shutdown routine for the computer of the pipe tester.

Referring to FIG. 6, routine B and, thus, routine J will be described. In step 109, processor 14 determines whether shoe and amplifier power supplies 17A and 17B and/or magnetizing coil power supply 7 are on. When none of the power supplies are on, processor 14 proceeds to step 111, otherwise, processor 14 proceeds to step 110. Processor 14 executes step 110 by deactivating one or both of relays 9 and 16 resulting in the appropriate power supply or supplies turning off. In step 111, processor 14 determines if any wall loss or flaw detection data remains stored in RAM 13. If no data exists, processor 14 proceeds to step 114, otherwise, processor 14 proceeds to step 112. Processor 14 executes steps 112 by saving any data stored in RAM 13 to HD 203. Processor 14 then executes step 113 which consists of compressing the data stored in HD 203 for archiving. In step 114, processor 14 displays the restart message illustrated in FIG. 10F. After displaying the restart message, processor 14 proceeds to step 115 and waits for the user to select the OK prompt which, in this preferred embodiment, is selected when the user depresses the ALT key in combination with the 0 key. Once the user selects the OK prompt, processor 14 exits routine B or J, whichever one was called, and returns to the original calling routine.

Figure 7:
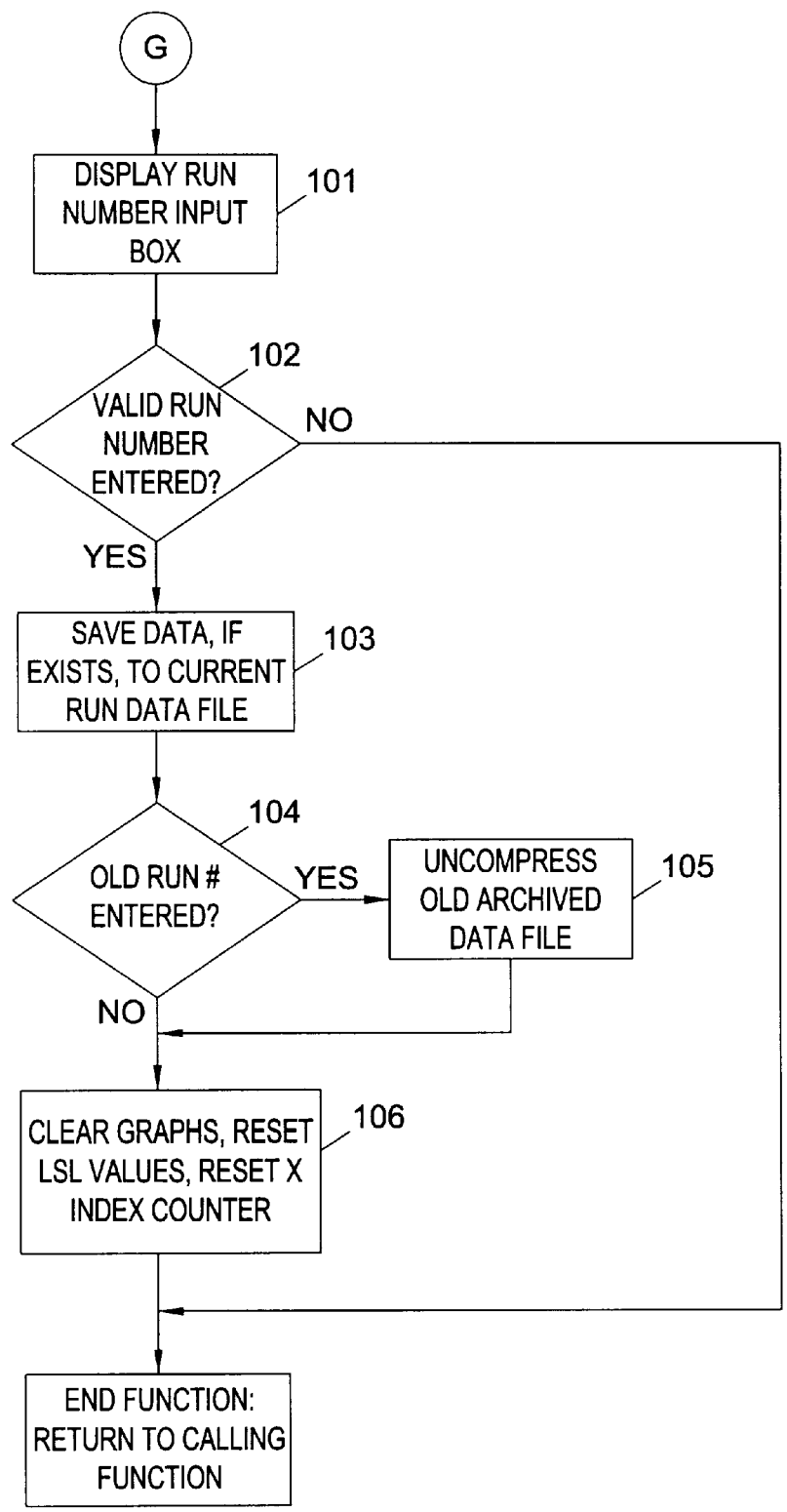
FIG. 7 is a flow chart illustrating the run number entrance routine for the computer of the pipe tester.

Referring to FIG. 7, routine G begins with processor 14 executing step 101 which consists of displaying the run number input box illustrated in FIG. 10D. The cursor appears in the run number input box so that the user may input a desired run number. In this preferred embodiment, the user selects the OK prompt by depressing the ALT key in combination with the 0 key. Similarly, the user selects the CANCEL prompt by depressing the ALT key in combination with the C key. If the user selects the CANCEL prompt, processor 14 returns to the routine from which routine G was called. When the user selects the OK prompt in combination with entering a run number, processor 14 proceeds to step 102 and determines whether the user entered a valid run number, which is either the next consecutive run number or a prior run number. If the input run number is invalid, processor 14 exits routine G and returns to the calling routine. If a valid run number was entered, processor 14 in step 103 saves to HD 203 any wall loss and flaw detection data signals that remain in RAM 13. When no wall loss and flaw detection data remains in RAM 13, processor 14 proceeds to step 104 and determines whether the user entered a prior run number. If the run number entered is not a prior one, processor 14 proceeds to step 106 and erases the wall loss and flaw detection graphs currently displayed on screen 200. Processor 14 further resets the wall loss high signal value, flaw high signal value, wall loss high signal channel, and flaw high signal channel, and X-index counter variables to 0 (described herein). Alternatively, if the run number is a prior one, processor 14 executes step 105 by uncompressing from HD 203 the wall loss and flaw detection data file associated with the entered prior run number to allow new wall loss and flaw signals to be appended to the end of that file. Processor 14 then executes step 106 as previously described. Processor 14 then exits routine G and returns to the calling routine.

Figure 8:
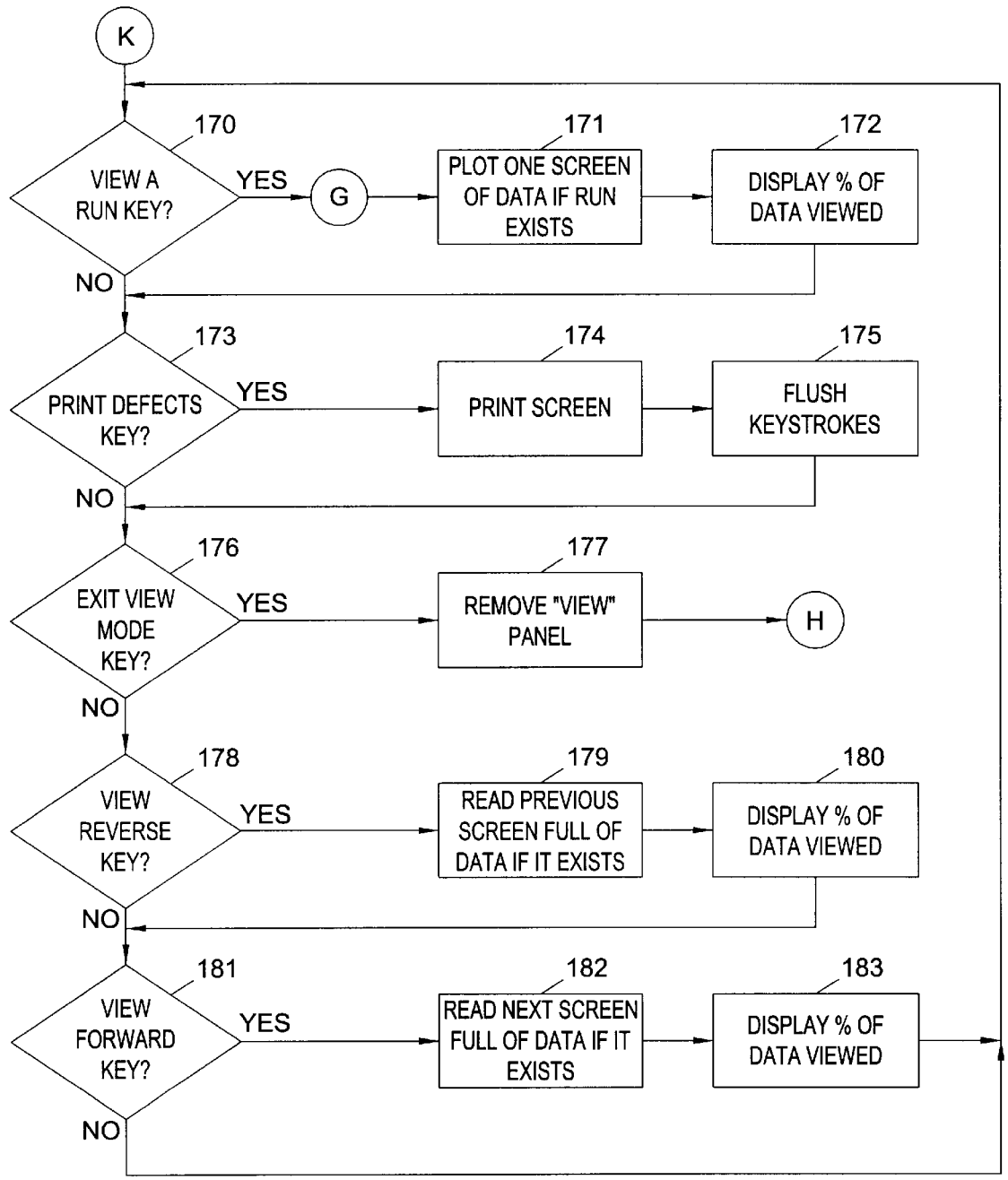
FIG. 8 is a flow chart illustrating the view data routine for the computer of the pipe tester.

Referring to FIG. 8, processor 14 begins routine K by executing step 170 which determines if the user has pressed the "view a run key". In this preferred embodiment, the user selects the "view a run key" by pressing the ALT key in combination with the V key. If the user elects not to view a run, processor 14 proceeds to step 173, otherwise, processor 14 executes routine G as previously described with reference to FIG. 7. Processor 14 then executes step 171 by plotting on screen 200 the first calculated interval of wall loss and flaw detection data signals obtained from routine G. In step 172, processor 14 displays on screen 200 the percentage of the total data signals that the first calculated interval represents.

In step 173, processor 14 determines if the user desires to print using printer 201 the wall loss and flaw detection graphs currently displayed on screen 200. In this preferred embodiment, the user selects the print option by pressing the ALT key in combination with the P key. If the user has not elected to print, processor 14 proceeds to step 176, otherwise, processor 14 proceeds to step 174. Processor 14 executes step 174 by downloading the display on screen 200 to printer 201 for printing. In step 175, processor 14 flushes the keyboard buffer of keyboard 18 so that any inadvertent key depressions will not affect the screen print.

In step 176, processor 14 determines if the user desires to exit the view mode. In this preferred embodiment, the user exits the view mode by pressing the ALT key in combination with the X key or by pressing the ESCAPE key. If the user elects not to exit the view mode, processor 14 proceeds to step 178, otherwise, processor 14 executes step 177 by removing the view panel. Processor 14 then executes routine H as previously described with reference to FIG. 3.

In step 178, processor 14 determines if the user desires to scroll backwards through the wall loss and flaw detection graphs displayed on screen 200. In this preferred embodiment, the user elects to scroll backwards by pressing the LEFT ARROW key. If the user elects not to scroll backwards, processor 14 proceeds to step 181, otherwise, processor 14 executes step 179 by displaying the previous calculated interval of wall loss and flaw detection data signals if any exist. In step 180, processor 14 displays on screen 200 the percentage of the total data signals that the currently displayed calculated interval represents.

In step 181, processor 14 determines if the user desires to scroll forwards through the wall loss and flaw detection graphs displayed on screen 200. In this preferred embodiment, the user elects to scroll forwards by pressing the RIGHT ARROW key. If the user elects not to scroll forwards, processor 14 returns to step 170, otherwise, processor 14 executes step 182 by displaying the next calculated interval of wall loss and flaw detection data signals if any exist. In step 183, processor 14 displays on screen 200 the percentage of the total data signals that the currently displayed calculated interval represents. Processor 14 then returns to step 170.

Figure 9:
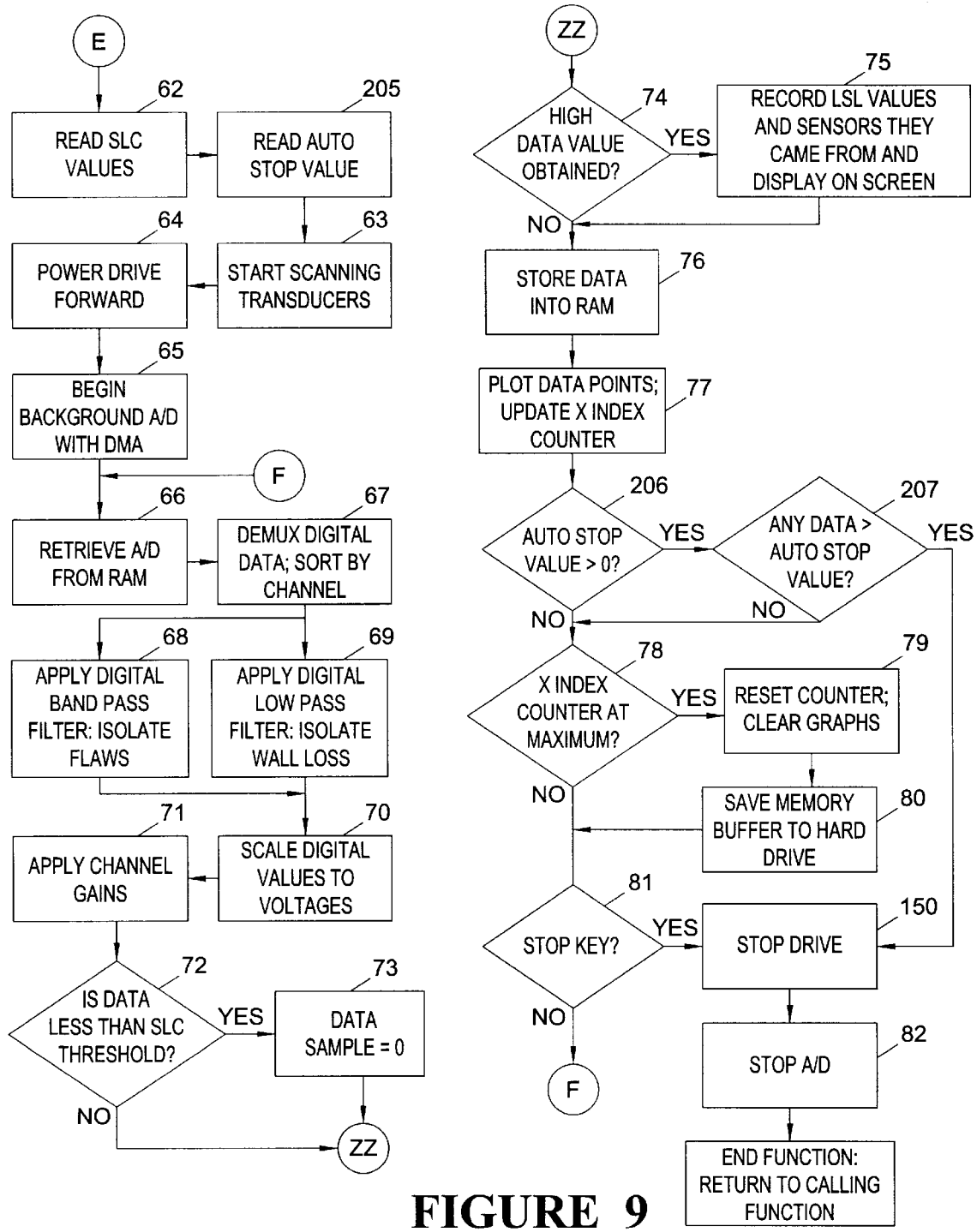
FIG. 9 is a flow chart illustrating the magnetic field data signal processing and analysis routine for the computer of the pipe tester.
Figure 10E:
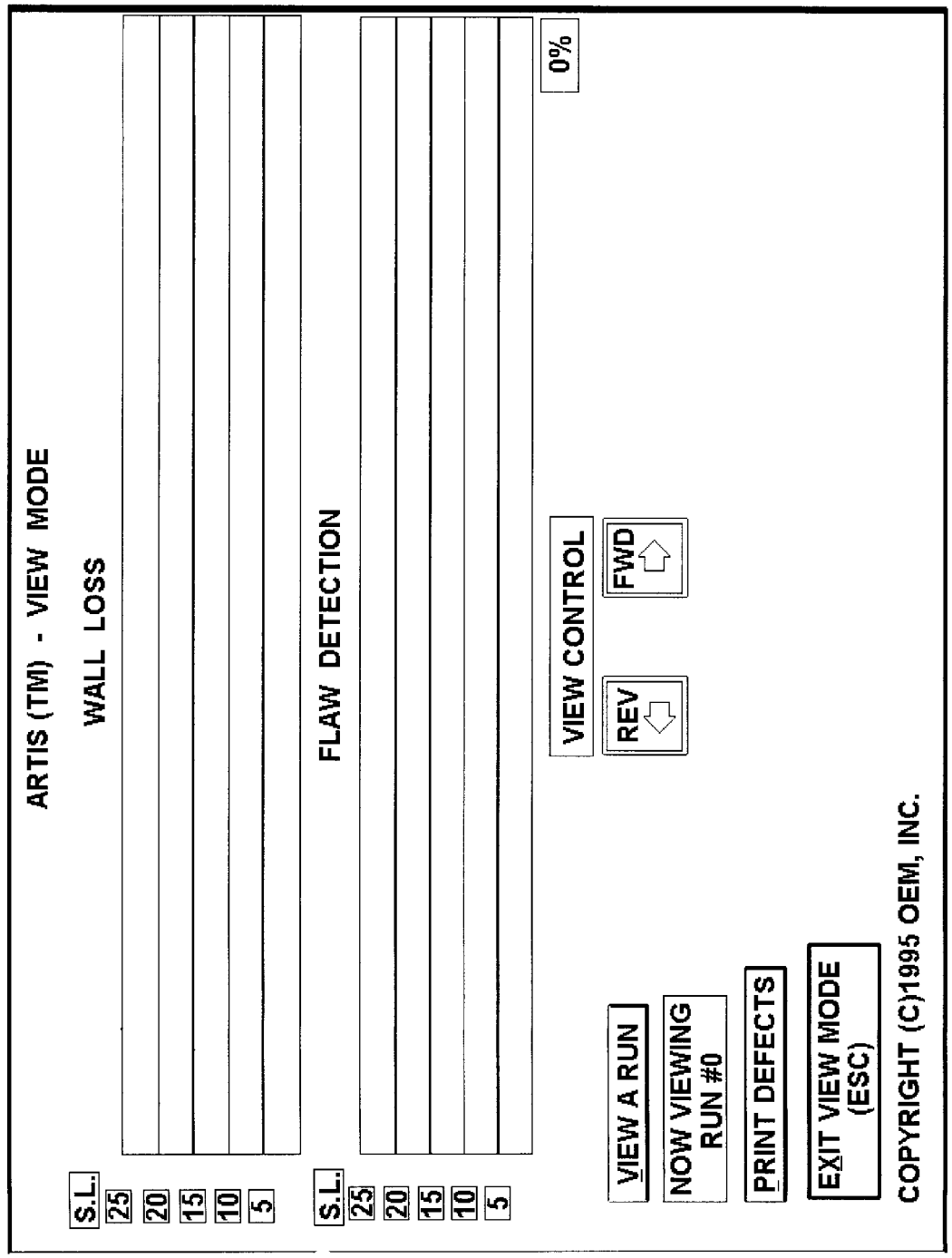
FIG. 10E illustrates the display depicted on the screen of the pipe tester.
Figure 10F:
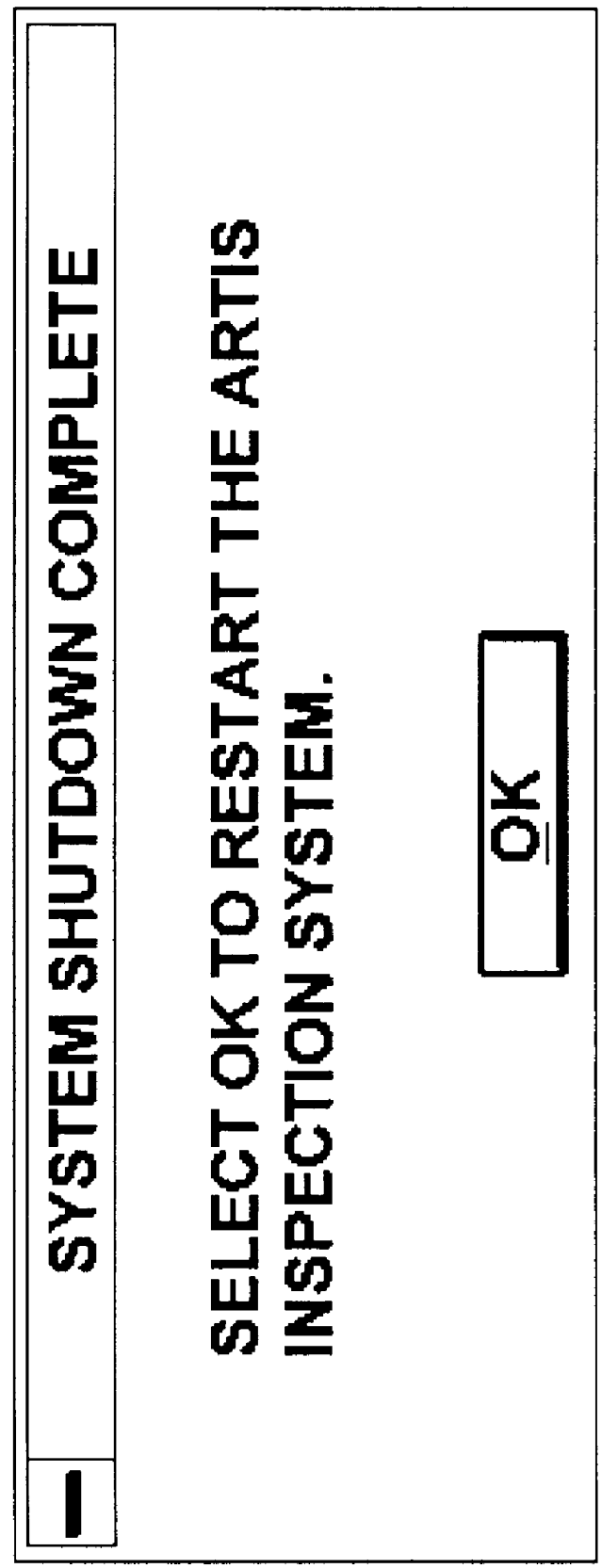
FIG. 10F illustrates the restart panel displayed to the user on the screen of the pipe tester.

Referring to FIG. 9, routine E which is executed by processor 14 to process and analyze the magnetic field data signals input from inspection shoes 2 will be described. In step 62, processor 14 reads into its memory the signal level control values selected by the user. The wall loss and flaw signals each have a separate signal level control value utilized to eliminate unnecessary magnetic field data measured by inspection shoes 2. Processor 14 utilizes the signal level control values to discard wall loss and flaw signals with a magnitude insufficient to produce meaningful results.

Figure 11:
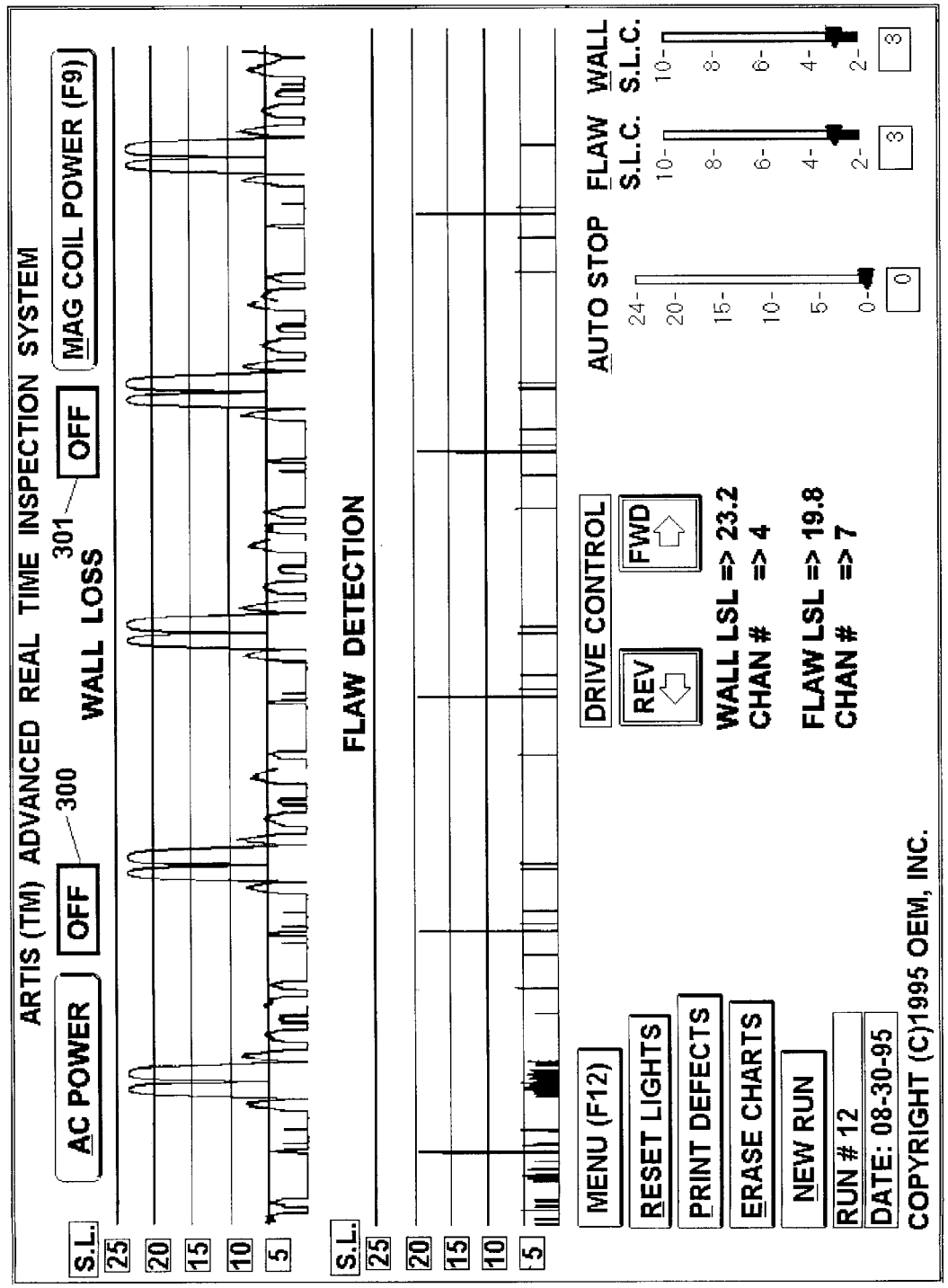
FIG. 11 illustrates the main display depicted on the screen of the pipe tester.

As illustrated in FIG. 11 of this preferred embodiment, the user elects to adjust the wall loss signal level control value by depressing the ALT key in combination with the W key. The user then presses the up arrow key to increase the wall loss signal level control value and the down arrow key to decrease that value. Similarly, the user elects to adjust the flaw signal level control value by pressing the ALT key in combination with the F key. The user then presses the up arrow key to increase the flaw signal level control value and the down arrow key to decrease that value.

In step 205, processor 14 reads into its memory the Auto Stop value selected by the user. In this preferred embodiment, the wall loss and flaw signals each utilize the same Auto Stop value. However, one of ordinary skill in the art will recognize that independent flaw and wall loss Auto Stop values may be used. Processor 14 utilizes the Auto Stop value to automatically stop drive unit 3 as soon as any flaw or wall loss signal magnitude becomes equal to or greater than the value selected by the user. This allows processor 14 to rapidly locate a defect along the length of the pipe and provides a fast means for the individual operating pipe tester 1 to mark the defect location.

As illustrated in FIG. 11 of this preferred embodiment, the user elects to adjust the Auto Stop value by depressing the ALT key in combination with the A key. The user then presses the up arrow key to increase the Auto Stop value and the down arrow key to decrease that value.

In step 63, processor 14 begins the sequential polling of each inspection shoes 2 or, alternatively, each linear Hall transducer during successive sampling periods which in this preferred embodiment are 134 milliseconds. The 134 millisecond sampling period was chosen based on processing speed, however, one of ordinary skill in the art will recognize that the sampling period can be decreased with increased processing speed. Processor 14 sequentially polls each of inspection shoes 2 or each linear Hall transducer during the first 134 millisecond sampling period to produce an array of magnetic field data signals in RAM 13. Each of inspection shoes 2 or linear Hall transducers has a separate channel to allow processor 14 to sort the array of magnetic field data signals according to inspection shoe or individual linear Hall transducer generating the data signal. After sequentially polling inspection shoes 2 or linear Hall transducers, processor 14 executes step 64 by propelling the inspection tool forward as previously described with reference to FIG. 3.

In step 65, DMA controller 12 continues to sequentially poll inspection shoes 2 or linear Hall transducers and handles the storing of the digitized magnetic field data signals in RAM 13. Thus, DMA controller 12 frees processor 14 from the above data storage task so that processor 14 may process the stored magnetic field data signals independently. Processor 14, therefore, provides real time evaluation of the magnetic field data signals because it does not have to oversee the task of storing subsequently measured signals.

DMA controller 12 stores the magnetic field data signals in RAM 13 in a matrix arranged such that each row represents the number of the sampling period with each sampling period occurring every 134 milliseconds, while each column represents a particular inspection shoe or individual linear Hall transducer. In storing the magnetic field data signal in the matrix, DMA controller 12 does not distinguish the incoming signals according to channel. Thus, the columns in the same matrix row are arranged according to A/D conversion number which means sequential A/D conversions for each channel are separated by the previous and following A/D conversions for all remaining channels.

While DMA controller 12 controls the storing of magnetic field data from successive sample periods, processor 14 executes step 66 by reading from RAM 13 the magnetic field data signals from the current sampling period. In step 67, processor 14 de-multiplexes the magnetic field data signals because those signals are arranged according to A/D conversion number. To de-multiplex the magnetic field data signals, processor 14 places those signals in a matrix format wherein each row represents the number of the sampling period and the columns are arranged in sequential sets according to channel number.

After sorting the digitized magnetic field data signals according to channel, processor 14 executes step 68 by applying a digital band pass filter to each digitized magnetic field data signal. The digital band pass filter applies Fast Fourier Transform algorithms to remove unwanted high and low frequencies. In this preferred embodiment, processor 14 implements a Butterworth filter using standard digital processing techniques well known to those of ordinary skill in the art.

Processor 14 applies a digital band pass filter because flaws in the pipe produce magnetic field data signals having a frequency expected in the band pass range. Consequently, the digital band pass filter isolates the band pass frequencies from the low frequencies associated with wall loss as well as the ultra high frequency spikes induced by power supply switching and other noise components. Thus, after band pass filtering, the magnetic field data signals provide a clear indication of where the flaws on the tested pipe reside.

In step 69, processor 14 concurrently applies a digital low pass filter to each digitized magnetic field data signal de-multiplexed in step 67. The digital low pass filter applies Fast Fourier Transform algorithms to remove unwanted high frequencies. In this preferred embodiment, processor 14 implements a Butterworth filter using standard digital processing techniques well known to those of ordinary skill in the art.

Processor 14 applies a digital low pass filter because wall loss in the pipe produces magnetic field data signals having a frequency expected in the low range. Consequently, the digital low pass filter isolates the low pass frequencies from the high frequencies associated with flaws as well as the ultra high frequency spikes induced by power supply switching and other noise components. Thus, after low pass filtering, the magnetic field data signals provide a clear indication of where wall loss on the tested pipe has occurred.

In using the above described digital band pass and low pass filters, processor 14 accomplishes digital frequency isolation between the detection of wall loss and flaws. Furthermore, digital filtering permits the determination of the actual frequency values of a particular wall loss or flaw. That allows for evaluation, classification and analysis according to frequency because individual wall loss and flaws produce unique frequency responses. Alternatively, analog filtering may be used to separate defects into the two categories of flaws and wall loss while allowing processor 14 to continue to perform digital frequency analysis on the two categories for defect evaluation, classification and analysis. This improves over analog methods as well as prior art computer implemented methods because neither perform such a frequency analysis. Additionally, the separation of the magnetic field data signals according to frequencies that indicate whether a wall loss or a flaw was detected allows for the elimination of an entire set of linear Hall transducers. Such an elimination improves over existing testers because it decreases costs, improves detection capability and sensitivity as well as simplifies the equipment required to perform testing.

In step 70, processor 14 processes the filtered magnetic field data signals to produce a scaled signal level of the voltage initially measured by one of inspection shoes 2 or an individual linear Hall transducer. During A/D conversion, A/D converter 15 converts each original voltage into a number between 0, which represents a signal level of 0, and 4096, which represents a maximum signal level. This preferred embodiment uses 4096 because there are 12 bits of resolution, however, one of ordinary skill in the art will recognize that additional processing power will allow greater resolution. Processor 14 must scale the digitized signals to produce a value suitable for display along the Y axis of the wall loss and flaw detection graphs. Processor 14 scales the magnetic field data signals by dividing each signal by 4096 to determine the ratio between each signal and the total resolution. Processor 14 then multiplies this ratio by the maximum signal level to produce the scaled signal level. Processor 14 then executes step 71 by applying any channel gains to the scaled magnetic field data signals. Processor 14 applies the channel gains by multiplying the calculated gain factors previously described with reference to FIG. 4 to the scaled magnetic field data signals.

In step 72, processor 14 compares each scaled wall loss magnetic field data signal with the wall loss signal level control value and each scaled flaw magnetic field data signal with the flaw signal level control value. When processor 14 determines either a scaled wall loss or flaw magnetic field data signal is less than its respective signal level control value, it executes step 73 by setting the scaled magnetic field data signal to 0. Conversely, if processor 14 determines either a scaled wall loss or flaw magnetic field data signal equals or exceeds its respective signal level control value, it proceeds directly to step 74.

In step 74, processor 14 determines the largest wall loss magnetic field data signal and flaw magnetic field data signal and corresponding inspection shoe or linear Hall transducer number measuring those signals. Processor 14 compares all of the wall loss magnetic field data signals until it determines the largest signal. In step 75, processor 14 then records the largest wall loss signal and corresponding inspection shoe or linear Hall transducer number measuring that signal. Processor 14 further displays on screen 200 the magnitude of the largest wall loss signal and the inspection shoe or linear Hall transducer measuring that signal.

Similarly, processor 14 compares all of the flaw magnetic field data signals until it determines the largest signal. In step 75, processor 14 then records the largest flaw signal and corresponding inspection shoe or linear Hall transducer number measuring that signal. Processor 14 further displays on screen 200 the magnitude of the largest flaw signal and the inspection shoe or linear Hall transducer measuring that signal.

In step 76, processor 14 stores in RAM 13 all processed wall loss and flaw magnetic field data signals. Processor 14 then executes step 77 by graphing the current sampling period of processed magnetic field data signals on the appropriate wall loss or flaw detection graph (see FIG. 11). Additionally, processor 14 increases the X-index counter by one 134 millisecond sampling period. In step 206, processor 14 checks the Auto Stop value. If the Auto Stop value is not greater than zero, processor 14 proceeds to step 78, otherwise, processor 14 proceeds to step 207. In step 207, processor 14 compares the current sampling period of processed magnetic field data to the Auto Stop value. If all of the processed magnetic field data is less than the Auto Stop value, processor 14 proceeds to step 78, otherwise, it proceeds to step 150. In step 150, processor 14 deactivates relay 10 thereby stopping the forward movement of the inspection tool, which places the inspection tool directly over the suspected defect. Processor 14 then executes step 82 by stopping DMA controller 12 thereby ending the input of A/D conversions to RAM 13. Processor 14 then proceeds to routine A and executes that routine as previously described with reference to FIG. 3.

In step 78, processor 14 determines whether the X-index counter has reached its maximum value. In this preferred embodiment, the X-index counter must reach a total of 15 seconds in 134 millisecond intervals to reach its maximum value. If the X-index counter has not reached its maximum value, processor 14 proceeds to step 81, otherwise, it executes step 79 by resetting the X-index counter to 0 and erasing the currently displayed wall loss and flaw detection graphs thereby permitting the display of more wall loss and flaw detection signals. Processor 14 then proceeds to step 80 and saves all the wall loss and flaw signals stored in RAM 13 to HD 203 to preserve those signals for later use.

In step 81, processor 14 determines if the user desires to end the testing run and stop the gathering and processing of the magnetic field data signals. In this preferred embodiment, the user presses the ESCAPE key to stop the current run. If processor 14 determines the user has pressed the ESCAPE key, it executes step 150 and step 82 as previously described.

When processor 14 determines the user does not desire to end the testing run, it re-enters routine E at routine F so that the next 134 millisecond sampling period of magnetic field data signals may be input from RAM 13 for processing as previously described. Accordingly, processor 14 continuously inspects and processes an entire ferrous pipe in real time to produce the wall loss and flaw detection graphs shown in FIG. 11. Those graphs provide the user with an indication of whether wall loss and flaws exist and where the large wall loss and flaws reside on the particular ferrous pipe tested.

Although the present invention has been described in terms of the foregoing embodiment, such description has been for exemplary purposes only and, as will be apparent to those of ordinary skill in the art, many alternatives, equivalents, and variations of varying degrees will fall within the scope of the present invention. That scope accordingly, is not to be limited in any respect by the foregoing description, rather, it is defined only by the claims that follow.

We claim:

1. An apparatus for inspecting a ferrous pipe to detect irregularities, comprising:
   means for inducing a magnetic field in the ferrous pipe;
   means for measuring changes in the induced magnetic field and for producing signals representative of those changes;
   means for processing said signals according to frequency to classify said signals by type of irregularity in the ferrous pipe; and
   means for processing said signals by comparing each of said signals to a first threshold value wherein, when a signal exceeds said first threshold value, said means for processing stops the inspection process to locate an irregularity in the ferrous pipe.

2. The apparatus according to claim 1 further comprising means for inputting user controls to said means for processing.

3. The apparatus according to claim 1 wherein said means for processing scales each of said signals.

4. The apparatus according to claim 1 wherein said means for processing applies a gain factor to each of said signals.

5. The apparatus according to claim 1 wherein said means for processing processes said signals according to a second threshold value wherein, when a signal is less than said second threshold value, said means for processing sets said signal to zero.

6. The apparatus according to claim 1 wherein said means for processing controls said means for inducing to vary the strength of the magnetic field.

7. The apparatus according to claim 1 wherein said means for inducing comprises a magnetizing coil.

8. The apparatus according to claim 1 further comprising means for displaying said frequency processed signals according to type of irregularity in the ferrous pipe.

9. The apparatus according to claim 8 wherein said means for displaying comprises a computer display screen.

10. The apparatus according to claim 8 wherein said means for displaying comprises a printer.

11. The apparatus according to claim 1 wherein said means for measuring changes in the induced magnetic field, comprises:
   at least one transducer for producing voltages corresponding to the changes in the magnetic field; and
   means for converting said voltages into digital signals.

12. The apparatus according to claim 11 wherein said at least one transducer is oriented parallel to the ferrous pipe and produces voltages corresponding to all irregularities represented by the changes in the magnetic field.

13. The apparatus according to claim 11 wherein said means for measuring changes in the induced magnetic field further comprises a buffer between said transducer and said means for converting.

14. The apparatus according to claim 13 wherein said means for measuring changes in the induced magnetic field further comprises a bank of capacitors between said buffer and said means for converting.

15. The apparatus according to claim 1 further comprising means for driving said means for inducing and means for measuring changes in the induced magnetic field and for producing signals representative of those changes.

16. The apparatus according to claim 15 wherein said means for processing controls the movement of said means for driving and stops said means for driving when a signal exceeds said first threshold value.

17. The apparatus according to claim 1 further comprising means for driving the ferrous pipe relative to said means for inducing and said means for measuring changes in the induced magnetic field and for producing signals representative of those changes.

18. The apparatus according to claim 17 wherein said means for processing stops said means for driving when a signal exceeds said first threshold value.

19. The apparatus according to claim 1 wherein said means for processing processes said signals according to frequency by applying a band pass filter to determine irregularities classified as flaws.

20. The apparatus according to claim 19 wherein said means for processing separates each flaw according to frequency to determine the type of flaw.

21. The apparatus according to claim 1 wherein said means for processing processes said signals according to frequency by applying a low pass filter to determine irregularities classified as wall losses.

22. The apparatus according to claim 21 wherein said means for processing separates each wall loss according to frequency to determine the type of wall loss.

23. The apparatus according to claim 1 wherein said means for processing comprises a computer.

24. The apparatus according to claim 23 wherein said computer, comprises:
   a random access memory;
   a direct memory access controller for handling the storage of said signals in said random access memory; and
   a processor that inputs said signals stored in said random access memory and processes said signals according to frequency to classify said signals by type of irregularity in the ferrous pipe.

25. The apparatus according to claim 24 wherein said computer further comprises non-volatile memory to store said signals processed according to frequency.

26. A method for inspecting a ferrous pipe to detect irregularities, comprising the steps of:
   inducing a magnetic field in the ferrous pipe;
   measuring changes in the induced magnetic field;
   producing signals representative of those changes;
   processing said signals according to frequency to classify said signals by type of irregularity in the ferrous pipe;
   processing said signals by comparing each of said signals to a first threshold value; and stopping the inspection process to locate an irregularity in the ferrous pipe when a signal exceeds said first threshold value.

27. The method according to claim 26 further comprising the step of displaying said frequency processed signals according to type of irregularity in the ferrous pipe.

28. The method according to claim 26 further comprising processing said signals according to a second threshold value wherein signals less than said second threshold value are set to zero.

29. The method according to claim 26 further comprising varying the strength of the magnetic field induced in the ferrous pipe.

30. The method according to claim 26 wherein said step of processing said signals according to frequency comprises the step of applying a band pass filter to determine irregularities classified as flaws.

31. The method according to claim 26 wherein said step of processing said signals according to frequency comprises the step of applying a low pass filter to determine irregularities classified as wall losses.

32. The method according to claim 26 wherein said step of displaying comprises the step of displaying said signals processed according to frequency on a computer display screen.

33. The method according to claim 26 wherein said step of displaying comprises the step of printing said signals processed according to frequency.

34. The method according to claim 26 further comprising scaling each of said signals.

35. The method according to claim 34 further comprising applying a gain factor to each of said signals.

36. The method according to claim 26 wherein the steps of measuring changes in the induced magnetic field and producing signals representative of those changes, comprises:
   producing voltages corresponding to the changes in the magnetic field; and
   converting said voltages into digital signals.

37. The method according to claim 36 wherein the steps of measuring changes in the induced magnetic field and producing signals representative of those changes further comprise buffering said voltages prior to conversion into digital signals.

38. The method according to claim 37 wherein the steps of measuring changes in the induced magnetic field and producing signals representative of those changes further comprises eliminating any DC component from said signals prior to conversion into digital signals.

39. The method according to claim 26 wherein said step of processing comprises:
   storing said signals in a random access memory utilizing a direct memory access controller; and
   sequentially processing said signals stored in said random access memory according to frequency to classify said signals by type of irregularity in the ferrous pipe.

40. The method according to claim 39 wherein said step of processing further comprises storing said signals processed according to frequency in non-volatile memory.

* * * * *